United States Patent [19]

Nakahara et al.

[11] Patent Number: 4,463,113

[45] Date of Patent: Jul. 31, 1984

[54] BIS-PHENOL PHOSPHATES AS CLARIFIERS FOR POLYOLEFIN RESINS

[76] Inventors: Yutaka Nakahara, 406-71, Minamishimoarai, Iwatsuki City, Saitama; Mitsuo Akutsu, 6-16-30, Aoto, Katsushika, Tokyo; Tohru Haruna, 969-4, Shimohideya, Okegawa City, Saitama; Masayuki Takahashi, 4-15-26, Midorimachi, Tokorozawa City, Saitama, all of Japan

[21] Appl. No.: 379,821

[22] Filed: May 20, 1982

[30] Foreign Application Priority Data

Jun. 25, 1981 [JP] Japan .................................. 56-98816

[51] Int. Cl.$^3$ ............................. C08K 5/52; C07F 9/21
[52] U.S. Cl. .................................... 524/117; 260/936; 524/119; 252/400 R
[58] Field of Search ................. 260/936; 524/117, 119; 252/400.2

[56] References Cited

FOREIGN PATENT DOCUMENTS 2049696 11/1980 United Kingdom ................. 260/936

Primary Examiner—Anton H. Sutto

[57] ABSTRACT

Bis-phenol phosphates, are provided, represented by the formula:

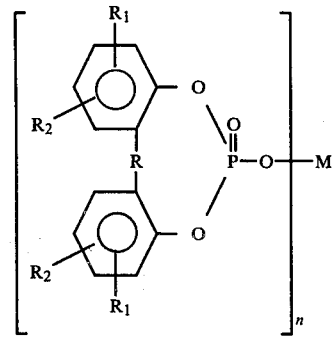

wherein:
R is selected from the group consisting of a carbon-to-carbon bond; thio sulfur —S—; and alkylidene

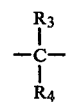

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to about twelve carbon atoms;
$R_1$ and $R_2$ are each selected from the group consisting of hydrogen, alkyl having from one to about eighteen carbon atoms; and cycloalkyl having from three to about twelve carbon atoms;
m is 0 or 1;
M is a metal atom which can be monovalent or polyvalent; and n is the valence of the metal atom M, ranging from one to about four;
useful to improve clarity of polyolefin resin compositions in an amount within the range from 0.005 to 5 parts by weight per 100 parts of resin.

32 Claims, No Drawings

BIS-PHENOL PHOSPHATES AS CLARIFIERS FOR POLYOLEFIN RESINS

Low density polyethylene has been known for many years to have a crystalline structure. Additional crystalline polymers such as high-density polyethylene, isotactic polypropylene, poly-1-butene, and poly-4-methylpentene have become available as a result of the development of the so-called stereospecific Ziegler-Natta catalyst system for the polymerization of alpha-olefins.

Such crystalline polymers possess special properties, not available in amorphous polymers, which are of steadily increasing commercial interest and importance. Certain properties of these crystalline polymers, particularly optical and strength properties, and processing characteristics, depend to a very significant extent upon the polymer microstructure.

According to C. J. Kuhre et al *SPE Journal*, 20, 1113–1119 (1964), rapid cooling from the molten state promotes a favorable microstructure by producing small spherulites and leads to improved clarity and toughness for polypropylene. However, quenching is, in general, applicable with maximum effect only to plastic fabricated with relatively thin section thickness, such as film or thin sheet. While some advantage can be gained in terms of improved microstructure by rapid cooling of plastic articles of relatively thick section, the effect is restricted by heat transfer limitations mainly to the surface shell of the plastic.

Certain additives promote the formation of smaller, more numerous spherulites in crystalline polymers. Use of such crystallization modifiers has the distinct and important advantage that their effect is not limited to plastic articles of this cross-section; a more favorable microstructure forms throughout the entire mass of the polymer.

As a crystalline polymer cools from the molten state, crystallites begin to form below the melting point, as supercooling progresses. The crystallites cluster about central nuclei to form spherulites which grow radially outward by addition of more crystallites as crystallization proceeds. Since the spherulites are birefringent, their growth can be readily observed with a polarizing microscope equipped with a hot stage.

Addition of small amounts of finely-ground, higher-melting polymers, such as polytetrafluoroethylene, nylon, polyhexamethylene terephthalate, or isotactic polyethylene in low-density polyethylene, and nylons 610 or 66 in nylon 11, result in improved transparency, similar to the improvement obtained by rapid quenching of thin films. This improvement is attributed to the smaller, more numerous spherulites promoted by nucleation, in the case of the polymeric additives, and by rapid cooling, which minimizes spherulite size in the case of quenching.

Certain inorganic additives, such as very fine silica, also show some nucleating effect in crystalline polymers. There are a number of other substances which are highly effective as nucleating agents in polypropylene.

Another example of these new nucleating agents are the metal salts of organic acids. Metals whose carboxylic acid salts are effective include sodium, magnesium, calcium, aluminum and titanium. The organic acid portion of the salt can be chosen from a variety of mono- or di-carboxylic acids. Examples of suitable monobasic acids are benzoic, cyclohexane, carboxylic, diphenyl acetic, and isonicotinic acids. Dicarboxylic acids such as succinic, adipic, sebacic, and phthalic acids give salts of similar activity. The efficiency of the nucleating agents varies with the choice of metal and acid used. Some of the more promising compounds are effective at concentrations well below 0.5% by weight.

Kuhre et al summarize the disclosures of P. Wijga in U.S. Pat. Nos. 3,207,735, 3,207,736, and 3,207,738, and M. Wales in U.S. Pat. Nos. 3,207,737 and 3,207,739, all patented Sept. 21, 1966.

Wijga U.S. Pat. No. 3,207,735 suggests cyclic monocarboxylic acids having the carboxyl group attached to a carbon atom of a five to six membered ring, and the corresponding anhydrides, referred to as "benzoic acid type compounds". The improvement is said to be obtained when the benzoic acid type compound is present as a liquid, dissolved or thoroughly dispersed in the polymer melt prior to the final crystallization thereof by cooling.

Wijga U.S. Pat. No. 3,207,736 suggests aliphatic, cycloaliphatic, and aromatic dicarboxylic or higher polycarboxylic acids and corresponding anhydrides.

Wijga U.S. Pat. No. 3,207,738 suggests terminal aliphatic monocarboxylic acids substituted with carbocyclic groups, also referred to as arylalkanoic acid-type compounds.

Wales U.S. Pat. No. 3,207,737 suggests salts of aluminum with certain carboxylic or polycarboxylic acids.

Wales U.S. Pat. No. 3,207,739 suggests salts of sodium and, to a lesser degree, other metals from Groups Ia and IIa of the Periodic Table, with certain carboxylic and polycarboxylic acids.

R. Harrington, U.S. Pat. No. 3,274,014 patented Sept. 20, 1966 discloses yarn compositions have incorporated a small amount of a metal monoalkyl or monoaryl phosphate, metal dialkyl phosphate, metal alkyl phosphonate, metal alkyl (alkyl phosphonate), or metal dialkyl phosphite resistant to ultraviolet light. Nothing is disclosed as to any effect on clarity or crystallization behavior of the yarn polymers, and since the yarns can be pigmented any such effect could have been overlooked.

K. Yamamoto Japanese Pat. No. 15,185/69 of July 15, 1969 discloses polypropylene compositions of regulated molecular weight containing organotin compounds as molecular weight modifying agents and esters of acids of phosphorus to prevent discoloration. All the disclosed esters are aliphatic esters, for example, dibutyl phosphite, dilauryl phosphite, triethyl phosphate, tributyl phosphate, and bis(2-ethylhexyl phosphate).

K. Shirayama Japanese Pat. No. 12,903/71 of Apr. 2, 1971 discloses crystalline polypropylene compositions of improved transparency and stiffness containing diphenylphosphinic acid represented by the formula

or its magnesium, calcium, sodium, or aluminum salts as a nucleating agent.

K. Shirayama Japanese Pat. No. 21,939/71 of June 22, 1971, discloses phenylphosphonic acid, phenyl phosphonous acid, phenyl arsonic acid and Na, Mg, Ca and Al salts of one of these acids as a nucleating agent for polypropylene.

K. Hamada U.S. Pat. No. 4,016,118 patented Apr. 5, 1977 discloses aliphatic polyolefins with increased transparency and reduced shrinkage containing 0.1 to 0.7% dibenzylidenesorbitol.

Ohzeki, Akutsu and Kawai, U.S. Pat. No. 4,258,142, patented Mar. 24, 1981, disclose that the clarity of polymers of alpha olefins having two to six carbon atoms can be improved by incorporating from 0.005 to 5 parts by weight per 100 parts by weight of olefin polymer of at least one phenyl phosphate having the formula:

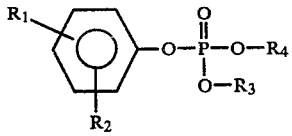

in which $R_1$ and $R_2$ are independently selected from the group consisting of a hydrogen atom, an alkyl group having one to eighteen carbon atoms, an alkoxy group having one to eighteen carbon atoms, a cycloalkyl group having five to twelve carbon atoms, a phenyl group, a phenoxy group, and a group

in which $R_5$ is a hydrogen atom or an alkyl group having one to eighteen carbon atoms; $R_3$ is selected from the group consisting of an alkyl group having one to eighteen carbon atoms,

and $R_4$; and $R_4$ is a hydrogen atom or a metal atom equivalent $M_{1/a}$ where $a$ is the valence of the metal atom M.

However, the compounds as prepared usually give off an unpleasant odor during processing, due perhaps to the presence of a phenol impurity, which is difficult to remove.

Also in accordance with this invention, a further improvement in clarity is obtained by using in combination with a phenyl phosphate clarifier as above defined from 0.3 to 3 parts by weight per part by weight of phenyl phosphate compound of a metal compound selected from metal salts of non-nitrogenous monocarboxylic acids having six to eighteen carbon atoms, metal oxides, metal hydroxides, metal chlorides, and metal carbonates. The amount of metal compound so used will not usually exceed 1 part per 100 parts of olefin polymer.

In accordance with the present invention, bis-phenol phosphates are provided, represented by the formula:

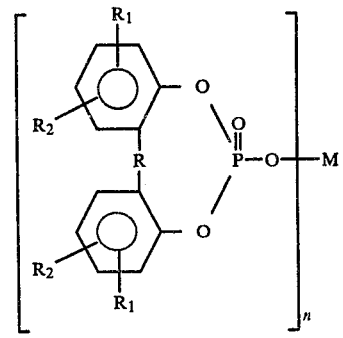

wherein:

R is selected from the group consisting of a carbon-to-carbon bond; thio sulfur —S—; and alkylidene

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to above twelve carbon atoms;

$R_1$ and $R_2$ are each selected from the group consisting of hydrogen, alkyl having from one to about eighteen carbon atoms; and cycloalkyl having from three to about twelve carbon atoms;

m is 0 or 1;

M is a metal atom which can be monovalent or polyvalent; and n is the valence of the metal atom M, ranging from one to about four;

The linking group R must form a ring including the phosphorus group:

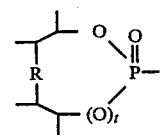

So far as is presently known, only a carbon-to-carbon bond, thiosulfur and alkylidene form such rings.

These compounds are useful to improve clarity of polyolefin resin compositions in an amount within the range from 0.005 to 5 parts by weight per 100 parts of resin.

These compounds have no odor, and are more effective, weight for weight, than the compounds of the Ohzeki et al U.S. Pat. No. 4,258,142.

The invention further provides α-olefin polymer compositions having improved clarity comprising a polymer of an α-olefin having two to six carbon atoms and an amount to improve clarity of at least one bis-phenol phosphate having the formula:

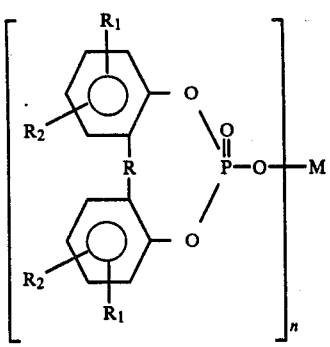

wherein:
R is selected from the group consisting of a carbon-to-carbon bond; thio sulfur —S—; and alkylidene

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to about twelve carbon atoms;
$R_1$ and $R_2$ are each selected from the group consisting of hydrogen, alkyl having from one to about eighteen carbon atoms; and cycloalkyl having from three to about twelve carbon atoms;
M is a metal atom; and
n is the valence of the metal atom M, ranging from one to about four.

The invention further provides stabilizer compositions for improving the clarity of polymers of α-olefins having two to six carbon atoms, comprising a heat or light stabilizer for α-olefin polymers and a compound of Formula (Ia) above.

Exemplary R alkylidene include methylidene, ethylidene, propylidene, isopropylidene, butylidene, isobutylidene, sec-butylidene, tert-butylidene, amylidene, hexylidene, heptylidene, octylidene, isooctylidene, 2-ethyl hexylidene, nonylidene and decylidene; cyclohexylidene, cycloheptylidene, methyl cyclohexylidene, ethyl cyclohexylidene, and cyclooctylidene.

Exemplary $R_1$ and $R_2$, $R_3$ and $R_4$ alkyl include methyl, ethyl, propyl, isopropyl, n-butyl, isobutyl, sec-butyl, t-butyl, amyl, t-amyl, hexyl, heptyl, octyl, 2-ethylhexyl, t-octyl, nonyl, decyl, undecyl, dodecyl, tridecyl, tetradecyl, pentadecyl, hexadecyl, heptadecyl and octadecyl.

Exemplary $R_1$ and $R_2$, $R_3$ and $R_4$ cycloalkyl include cyclopropyl, cyclobutyl, cyclopentyl, methylcyclopentyl, cyclohexyl, methylcyclohexyl, cycloheptyl, cyclooctyl and cyclododecyl.

Exemplary M monovalent metals include Li, Na, Ki; exemplary bivalent metals include Be, Ca, Sr, Ba, Zn, and Cd;

Exemplary trivalent and tetravelent metals include Al, Ge, Sn, Pb, Ti, Zr, Sb, Cr, Bi, Mo, Mn, Fe, Co and Ni. Among these metals, the alkali metals such as Li, Na and K and the alkaline earth metals such as Mg, Ca, Sr and Ba are preferred.

Typical examples of compounds of the above formula I are as follows:

Bis-Phenol Phosphates

1. 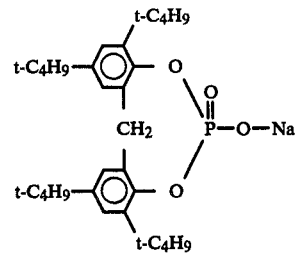

2. 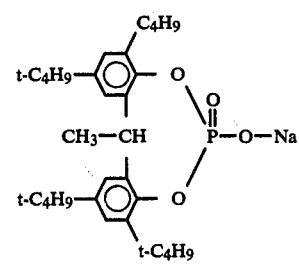

3. 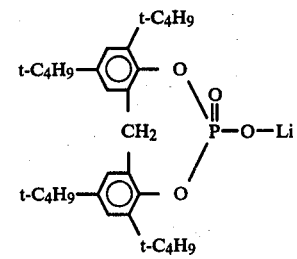

4. 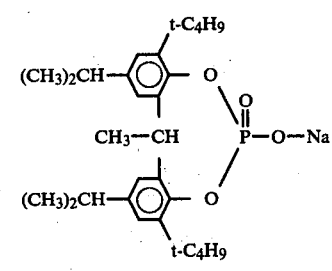

5. 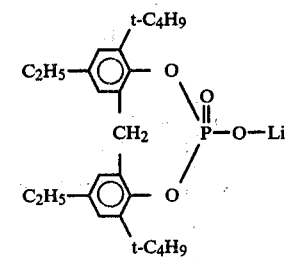

-continued

Bis-Phenol Phosphates

6. [Structure: bis(2-methyl-6-(1-methylcyclohexyl)phenyl) methylene phosphate potassium salt]

7. [Structure: bis(4-methyl-6-tert-butyl-2-thio-phenyl) phosphate calcium salt]₂ Ca 8. [Structure: bis(4-tert-butyl-6-tert-butyl-2-thio-phenyl) phosphate magnesium salt]₂ Mg 9. [Structure: bis(4-tert-octyl-2-thio-phenyl) phosphate magnesium salt]₂ Mg 10. [Structure: bis(2,4-dimethyl-6-hydroxyphenyl) butylidene phosphate sodium salt, with C₃H₇—CH bridge]

11. [Structure: bis-phenol cyclohexylmethylene phosphate sodium salt]

-continued

Bis-Phenol Phosphates

12. [Structure: bis(2,4-dimethylphenyl) t-C₈H₁₇—CH phosphate sodium salt]

13. [Structure: bis(2,6-di-tert-butyl-4-methylphenyl) methylene phosphate barium salt]₂ Ba 14. [Structure: bis(2-tert-butyl-4-methylphenyl) methylene phosphate sodium salt]

15. [Structure: 2,2'-biphenyl (3,3'-di-tert-butyl-5,5'-dimethyl) phosphate sodium salt]

16. [Structure: bis(2,4-di-tert-butyl-6-tert-butylphenyl) biphenyl phosphate calcium salt]₂ Ca 17. [Structure: bis(2-sec-butyl-4-tert-butylphenyl) ethylidene (CH₃—CH) phosphate sodium salt]

| Bis-Phenol Phosphates |
|---|
| 18. 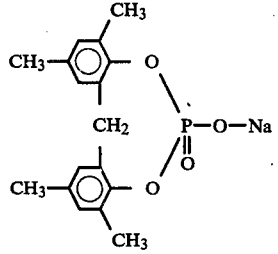 |
| 19. 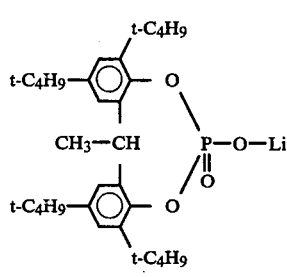 |
| 20. 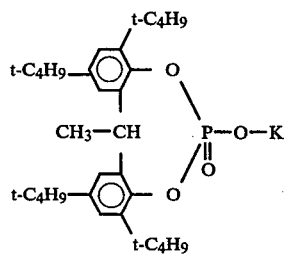 |
| 21. 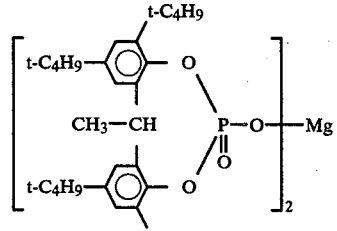 |
| 22. 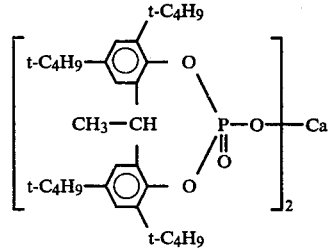 |

The α-olefin polymers whose clarity is improved in accordance with this invention by incorporating therein a bisphenol phosphoric acid metal salt are homopolymers and copolymers of α-olefins, including polyethylene, polypropylene, polybutene-1, poly-3-methylbutene, poly-4-methylpentene, 1,2-polybutadiene; copolymers of ethylene in major proportions with minor proportions of propylene, 1-butene, 1-hexene, vinyl acetate and vinyl chloride; copolymers of propylene in major proportions with minor proportions of ethylene, 1-butene, or vinyl chloride; and copolymers of butylene, 3-methyl butene, 4-methyl pentene, and 1,2-butadiene with minor proportions of such monomers.

The bis-phenol phosphate compounds according to this invention are clarifiers but not olefin polymer heat and/or light stabilizers. However, the bis-phenol phosphate compounds according to this invention do not adversely affect heat and light stability of α-olefin polymers, and can be used together with known heat and light stabilizers for α-olefin polymers in conventional concentrations.

The bis-phenol phosphate compounds can be combined with conventional heat stabilizers such as phenolic antioxidants, polyvalent metal salts or organic acids, organic phosphites, thioethers and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

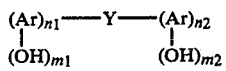

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

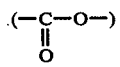

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

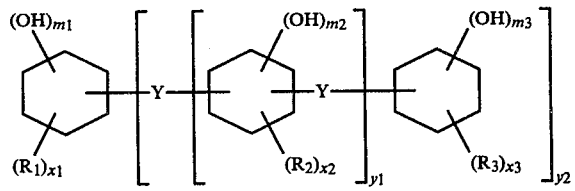

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

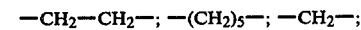

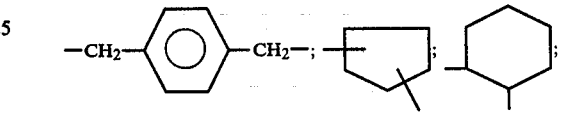

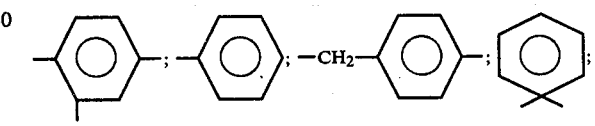

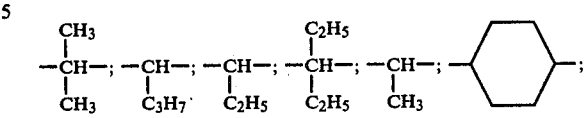

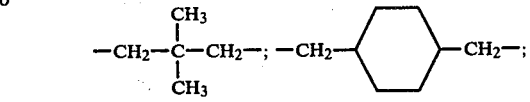

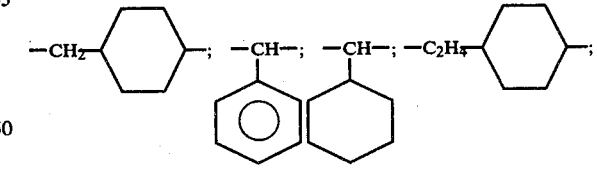

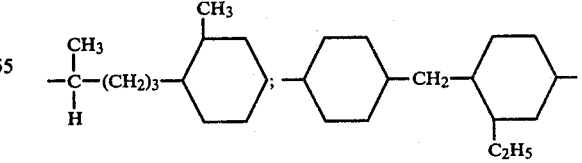

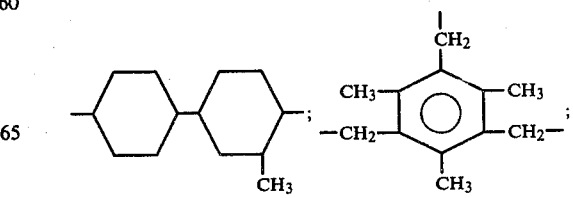

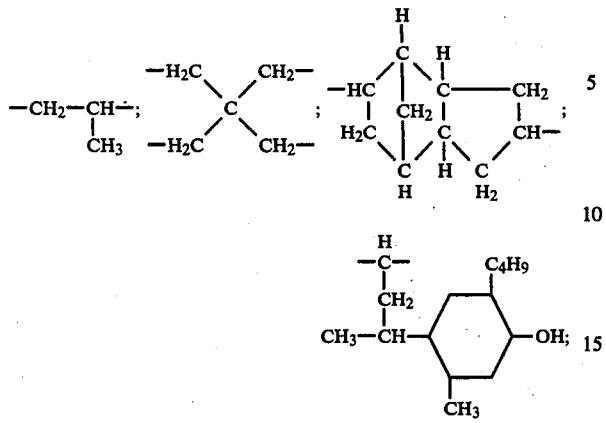

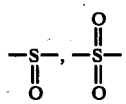

(2) Y groups where only atoms other than carbon link the aromatic rings, such as
—O—, —S—, $$-S-, \quad -\overset{O}{\underset{O}{\overset{\|}{S}}}-$$

and —(S)$_x$— where x is a number from one to ten;

(3) Y groups made up of more than a single atom including both carbon and other atoms linking the aromatic nuclei, such as:

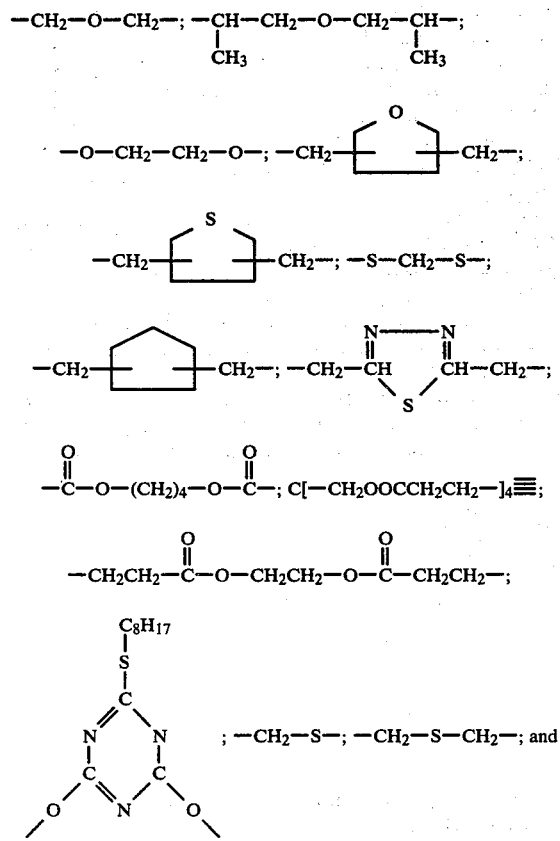

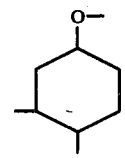

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate 2,6-di-tert-butyl-4-methyl phenyl, 2-tert-butyl-4-methoxy phenol, 2,4-dinonyl bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methylbenzyl)-4-methyl-phenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methylbenzyl)-4-methyl-phenol, 4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl)ethane, 2,2'-methylene-bis-(4-octyl-phenol), 4,4'-propylene-bis-(2-tert-butyl-phenol), phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m- tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-di-chlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)-propionate, distearyl-3,5-di-t-butyl-4-hydroxybenzyl-phosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4- hydroxy phenyl)-propane, methylene-bis-(p-cresol), 4,4'-benzylidene bis (2-tertiary-butyl-5-methyl-phenol), diene tri-(2-tert-butyl-4-methyl-phenol) of the formula:

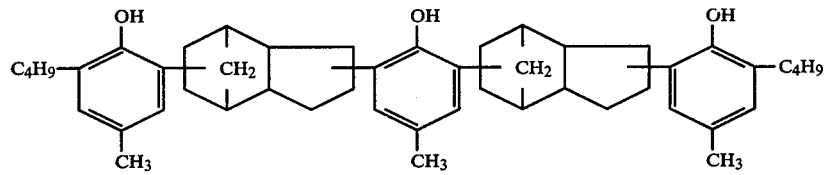

4,4'-cyclo-hexylidene 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butylphenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methylbenzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid] glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

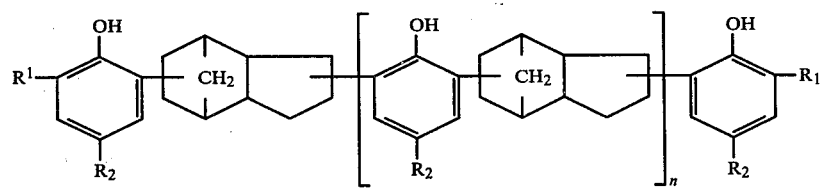

in which
R₁ and R₂ are lower alkyl, and can be the same or different, and
n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopenta- The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenoic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicyclic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

$$R_1-O-P-O-R_3$$
$$|$$
$$O$$
$$|$$
$$R_2$$

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

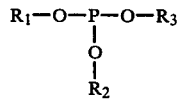

in which
$R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$; $R_5$ is hydrogen or a cation, in the case of the acid phosphites.

Also useful organic triphosphites are mixed heterocyclic-open chain phosphites of the type:

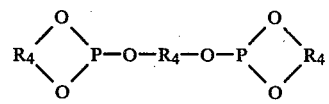

More complex triphosphites are formed from trivalent organic radicals, of the type:

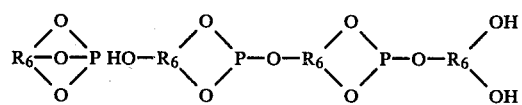

in which
$R_6$ is a trivalent organic radical of any of the types of $R_1$ to $R_5$, inclusive, as defined above.

A particularly useful class of complex triphosphites are the tetraoxadiphosphaspiro undecanes of the formula:

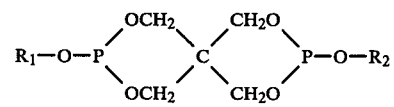

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

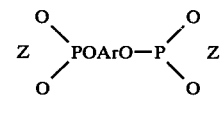

or

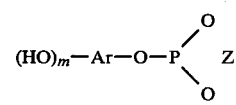

in which Ar is a mono or bicyclic aromatic nucleus and m is an integer of from 0 to about 5. $Z$ is one or a plurality of organic radicals as defined above for $R_1$ to $R_6$, taken singly or together in sufficient number to satisfy the valences of the two phosphite oxygen atoms.

One or both $Z$ radicals is also hydrogen, in the case of the acid phosphites, and can include additional bicyclic aromatic groups of the type $(HO)_m-Ar$.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri (2-cyclohexylphenyl) phosphite), tri-α-naphthyl phosphite, tri (phenylphenyl) phosphite, tri(2-phenylethyl) phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro (5,5)-undecane, 3,9-di (isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di (methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy) ethyloxy group has an average molecular weight of 350),3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol)) isooctyl phosphite, mono(4,4'-thio-bis(2-tertiary-butyl-5-methyl-phenol)) di-phenyl phosphite, tri-(4,4'-n-butylidene-bis(2-tertiary-butyl-5-methyl-phenol)) phosphite, (4,4'-benzylidene-bis(2-tertiary-butyl-5-methyl-phenol)) diphenyl phosphite, isooctyl 2,2'-bis(-parahydroxyphenyl) propane phosphite, decyl 4,4'-n-butylidene-bis (2-tertiary-butyl-5-methylphenol) phosphite, tri-4,4'-thio-bis (2-tertiary-butyl-5-methylphenol phosphite, 2-ethylhexyl-2,2'-methylene-bis(4-methyl-6,1'-methylcyclohexyl) phenol phosphite, tri(2,2'-bis-(para-hydroxyphenyl) propane) phosphite, tri(4,4'-thio-bis(2-tertiary-butyl-5-methyl-phenol) phosphite, isooctyl-(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl) diphosphite, tetra-isooctyl-4,4'-thio-bis (2-tertiary-butyl-5-methylphenyl) diphosphite, 2,2'-methylene-bis(4-methyl-6,1'-methyl cyclohexyl phenyl) polyphosphite, isooctyl-4,4'-isopropylidene-bis-phenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidene bis (2-tertiary-butyl-5-methylphenyl) diphosphite, tetra-tridecyl-4,4'-isopropylidene bisphenyl diphosphite, hexa-tridecyl butane-1,1,3-tris(2'-methyl-5'-tertiary-butylphenyl-4') triphosphite.

Exemplary acid phosphites are di(phenyl) phosphite, monophenyl phosphite, mono(diphenyl) phosphite, dicresyl phosphite, di-(o-isooctylphenyl) phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl) phosphite, monocyclohexyl phosphite, dicyclohexyl phosphite, di(2-cyclohexyl phenyl) phosphite, di-α-naphthyl phosphite, diphenyl phenyl phosphite, di(diphenyl) phosphite, di-(2-phenyl ethyl) phosphite, dibenzyl phosphite, monobenzyl phosphite, n-butyl cresyl phosphite and didodecyl phosphite, cresyl phosphite, t-octylphenyl phosphite, ethylene phenyl phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol)) phosphite, (4,4'-thio-bis(2-tertiary-butyl-5-methylphenol)) phenyl phosphite, bis(4,4'-n-butylidene-bis(2-tertiary-butyl-5-methylphenyl)) phosphite, mono(4,4'-benzylidene-bis(2-tertiary-butyl-5-methylphenol)) phosphite, mono(2,2'-bis-(parahydroxyphenyl) propane) phosphite, mono(4,4'-butylidene-bis(2-tertiary-butyl-5-methylphenol) phosphite, bis(4,4'-thio-bis(2-tertiary-butyl-5-methylphenol)) phosphite, mono-2-ethylhexyl-mono-2,2'-methylene-bis(4-methyl-6,1'-methylcyclohexyl) phenol phosphite, bis (2,2'-bis(para-hydroxyphenyl)propane)phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl-5-methylphenyl) diphosphite, triisooctyl-4,4'-thio-bis(2-tertiary-butyl-5-methylphenyl) diphosphite, bis(2,2'-methylene-bis(4-methyl-6,1'-methyl cyclohexyl phenyl)) phosphite, isooctyl-4,4'-isopropylidene-bis-phenyl phosphite, monophenyl mono(2,2'-methylene-bis(4-methyl-6,1'-methyl-cyclohexyl)) triphosphate, di-tridecyl-4,4'-oxydiphenyl diphosphite, di-n-dodecyl-4,4'-n-butylidene-bis(2-tertiary-butyl-5-methylphenyl) diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

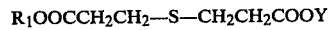

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical R₂, which can be the same as or different from the R₁ radical, (c) a polymeric chain of n thiodipropionic acid ester units:

—XO[OCCH₂CH₂SCH₂CH₂COOXO]ₙOCCH₂CH₂—S—CH₂CH₂COOZ where Z is hydrogen, R₂ or M, n is the number of thiodipropionic acid ester units in the chain, and X is a bivalent hydrocarbon group of the type of R₁, that is, alkylene, alkenylene, cycloalkylene, mixed alkylene-arylene and mixed alkylene-cycloalkylene radicals; hydroxyalkylene and hydroxyalkyloxy-alkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
(a) R₁OOCCH₂CH₂SCH₂CH₂COOH
(b) R₁OOCCH₂CH₂SCH₂CH₂COOR₂
(c) R₁O[OCCH₂CH₂SCH₂CH₂COOX—O]ₙOCCH₂CH₂SCH₂CH₂COOZ
(d) R₁OOCCH₂CH₂SCH₂CH₂COOM In the above formulae R₁ and R₂, M, X and Z are the same as before and the value of n₁ can range upwards from 1, but there is no upper limit on n₁ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, R₂ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

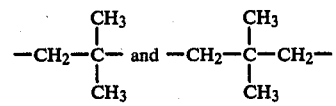

arylene radicals such as phenylene

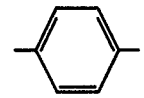

methylenephenylene

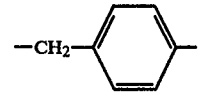

dimethylene phenylene

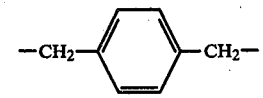

and alicyclylene such as cyclohexylene

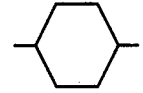

and cyclopentylene

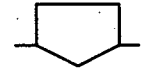

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

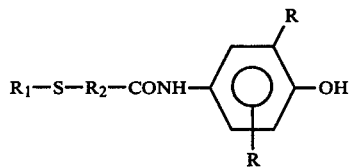

R is alkyl of one to eight carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

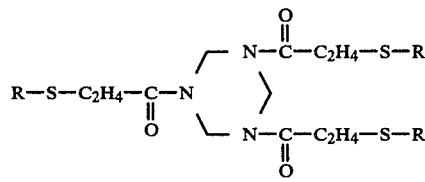

R is alkyl of eight to eighteen carbon atoms.

(3) Bis-thioalkanoic acid amides of Yamamoto et al Japanese Pat. No. 23,765/68 having the formula:

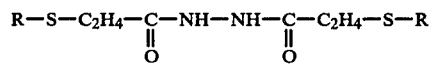

R is alkyl of more than six carbon atoms, aryl or aralkyl.

(4) Bis-thioalkylanoic acid amides of Ozeki et al Japanese Pat. No. 26,184/69 having the formula:

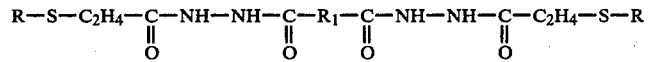

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

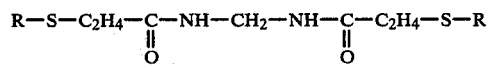

R is alkyl of more than six carbon atoms, aryl, or aralkyl.

(6) Thioalkanoic acid amide derivatives of Minagawa et al, published Japanese application No. 106,484/74 having the formula:

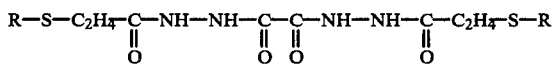

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

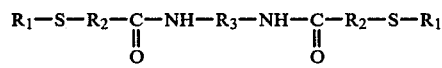

wherein:
$R_1$ is alkyl having from one to about fifty carbon atoms;
$R_2$ is alkylene having from one to about three carbon atoms; and
$R_3$ is alkylene having from about two to about twelve carbon atoms.

Examples of conventional light stabilizers that can be included with bis-phenol phosphates, of the invention include hydroxybenzophenones such as 2-hydroxy-4-methoxybenzophenone, 2-hydroxy-4-n-octoxy benzophenone, and 2,4-dihydroxybenzophenone; benzotriazoles such as 2-(2-hydroxy-5-methylphenyl) benzotriazoles, 2-(2-hydroxy-3-t-butyl-5-methylphenyl)-5-chloro benzotriazole, 2-(2-hydroxy-3,5-di-t-butyl phenyl)-5-chloro benzotriazole, and 2-(2-hydroxy-3,5-di-t-amyl phenyl) benzotriazole; benzoates such as phenyl salicylate, and 2,4-di-t-butyl phenyl-3,5-di-t-butyl-4-hydroxy phenylbenzoate; nickel compounds such as nickel-2,2'-thiobis (4-t-octyl phenolate), and nickel-monoethyl (3,5-di-t-butyl-4-hydroxybenzyl) phosphonate; substituted acrylonitriles such as methyl-α-cyano-β-methyl-β-(p-methoxy phenyl) acrylate; oxalic anilides such as N-2-ethyl phenyl-N'-2-ethoxy-5-t-butyl phenyl oxalic diamide and N-2-ethyl phenyl-N'-2-ethoxyphenyl oxalic diamide; and 2,2,6,6-tetraalkyl piperidines such as bis(2,2,6,6-tetramethyl-4-piperidyl) sebacate.

This bis-phenol phosphate compounds according to this invention and any desired heat and light stabilizers for α-olefin polymers can be formulated as a stabilizer composition and marketed as such, if desired in solution in an inert solvent, or formulated as a simple mixture for incorporation into the olefin polymer by the polymer manufacturer or converter. The clarifier compounds and any other stabilizers can also be individually incorporated in the polymer. The incorporation is by any suitable mixing equipment, such as a mill, a Banbury mixer, or an extruder-pelletizer system. Mixing is continued until the resin composition is substantially uniform, and can be removed to shaping equipment for fabrication into desired products, such as by calendering, extrusion, or injection-molding.

The α-olefin polymer can be converted into any physical form, including (for example) filaments, yarns, films, sheets, molded articles, latex, and foam.

A sufficient amount of the bis-phenol phosphate or combination thereof with a heat and/or light stabilizer α-olefin used to improve the resistance of the polymer to improve clarity and resist deterioration in physical properties, including, for example, discoloration, reduction in melt viscosity and embrittlement, under the conditions to which the polymer will be subjected. Very small amounts are usually adequate. Amounts within the range from about 0.005 to about 10% total stabilizers including from about 0.005 to about 5% bis-phenol phosphate by weight of the polymer are satisfactory. Preferably, from 0.01 to 2% bis-phenol phosphate is employed for optimum improvement in clarity.

Inasmuch as all components are solids, the stabilizer systems of the invention are readily rendered in solid particulate form, comprising a blend of:
(a) bis-phenol phosphate in an amount of from about 10 to about 35 parts by weight; and optionally;
(b) a phenolic antioxidant in an amount from about 10 to about 35 parts by weight; and/or
(c) other heat or light stabilizers in an amount of from about 10 to about 35 parts by weight.

The following Examples represent preferred embodiments of α-olefin polymer compositions whose clarity is improved by the bis-phenol phosphate compounds shown by formula in the Tables.

EXAMPLES 1 TO 12

Polypropylene compositions were prepared having the following formulation:

| Ingredient | Parts by Weight |
|---|---|
| Unstabilized polypropylene resin (Profax 6501) | 100 |
| Tetrakis (methylene-3-(3,5-di-t-butyl-4-hydroxyphenyl)propionate)methane | 0.1 |
| Dilaurylthiodipropionate | 0.2 |
| Bis-phenol phosphate, as shown in Table I | 0.2 |

The ingredients were kneaded at 180° C. for five minutes on a two-roll mill, and the compression-molded for five minutes at 180° C. and 250 kg/cm², then cooled to 60° C. rapidly to give specimens 1.0 mm thick.

The haze value according to ASTM D-1003-61, and Izod impact value at 20° C. were determined for each specimen, and the results are shown in Table I.

TABLE I

| Example No. | Bis-Phenol Phosphate, | Haze value (%) | Izod impact strength value (Kg. cm/cm²) |
|---|---|---|---|
| Control 1 | None | 83 | 7.5 |
| Control 2 | Al—tri(p-t-butyl-benzoate) | 69 | 10.1 |
| Control 3 | Di—Na—p-t-butyl-phenyl phosphate (No. 31 of U.S. Pat. No. 4,258,142) Phosphates | 58 | 13.2 |
| 1 | [structure: t-C4H9 / t-C4H9 phenyl with CH2 bridge to phenyl with t-C4H9 / t-C4H9, P(=O)—O—Na] | 42 | 16.6 |
| 2 | [structure: t-C4H9 / t-C4H9 phenyl with CH3—CH bridge to phenyl with t-C4H9 / t-C4H9, P(=O)—O—Na] | 43 | 16.8 |
| 3 | [structure: t-C4H9 / t-C4H9 phenyl with CH2 bridge to phenyl with t-C4H9 / t-C4H9, P(=O)—O—Li] | 45 | 16.0 |
| 4 | [structure: (CH3)2CH / t-C4H9 phenyl with CH3—CH bridge to phenyl with (CH3)2CH / t-C4H9, P(=O)—O—Na] | 43 | 16.7 |
| 5 | [structure: C2H5 / t-C4H9 phenyl with CH2 bridge to phenyl with C2H5 / t-C4H9, P(=O)—O—Li] | 45 | 16.2 |

TABLE I-continued

| Example No. | Structure | Haze value (%) | Izod impact strength value (Kg. cm/cm$^2$) |
|---|---|---|---|
| 6 | (3,5-dimethyl-cyclohexyl-methyl bis-phenol phosphate, K salt) | 47 | 16.1 |
| 7 | (2,6-dimethyl-4-isobutyl bis-phenol phosphonate, Na salt) | 43 | 16.8 |
| 8 | (cyclohexyl bis-phenol phosphonate, Na salt) | 46 | 16.0 |
| 9 | (2,6-dimethyl-4-t-octyl bis-phenol phosphonate, Na salt) | 44 | 16.5 |
| 10 | (2-methyl-4,6-di-t-butyl bis-phenol methylphosphonate, Na salt) | 42 | 17.1 |
| 11 | (2-methyl-4,6-di-t-butyl bis-phenol phosphate, Na salt) | 43 | 17.1 |
| 12 | (2-sec-butyl-4-t-butyl bis-phenol ethylidene phosphinate, Na salt) | 43 | 16.5 |

It is apparent from the above results that the bis-phenol phosphates, phosphonates and phosphinates of the invention are superior to the Controls.

Control 3 is the best compound in Table 2 of Ohzeki et al U.S. Pat. No. 4,258,142, and is superior to conventional clarifiers such as Al-tri(p-t-butyl benzoate). The difference in the results shown in Table I above and in Table 2 of U.S. Pat. No. 4,258,142 is due to the amount added; the amount above is 0.2 part, and the amount in U.S. Pat. No. 4,258,142 is 0.3 part. This shows that the compounds of this invention can improve the clarity of polyolefins in a smaller amount than the Ohzeki et al compounds. Moreover, Control 3 gave off an odor during processing caused by a small amount of unreacted phenol impurity. The compounds of this invention, however, gave off no odor during processing.

EXAMPLES 13 TO 20

Polypropylene resin compositions were prepared having the following formulation:

| Ingredient | Parts by Weight |
|---|---|
| Unstabilized polypropylene (Profax 6501) | 100 |
| Stearylbeta (3,5-di-t-butyl-4-hydroxyphenyl)propionate | 0.1 |
| Distearyl thiodipropionate | 0.2 |
| Bis-phenol phosphate, shown in Table II | 0.25 |

The ingredients were mixed for five minutes in a mixing and grinding machine, extruded and pelletized by an extruder at 220° to 250° C., rate of rotation 20 rpm, and then converted to a sheet of 100×40×1 mm by injection-molding at 220° to 250° C., under an injection pressure of 475 kg/cm$^2$ and a molding pressure of 570 kg/cm$^2$, with a cooling time of ten to thirty seconds.

The haze value and Izod impact strength value were determined, and the results obtained are shown in Table II.

TABLE II

| Example No. | Bis-Phenol Phosphate, | Haze value (%) | Izod impact strength value (Kg. cm/cm$^2$) |
|---|---|---|---|

TABLE II-continued

| Example No. | Structure | Haze value (%) | Izod impact strength value (Kg. cm/cm²) |
|---|---|---|---|
| Control 1 | None | 79 | 7.8 |
| Control 2 | Ca—2,4-di-t-butylphenyl phosphate (No. 26 of U.S. Pat. No. 4,258,142) | 58 | 11.2 |
| | Phosphates | | |
| 17 | Na salt of bis(2,4-di-t-butylphenyl)methylene phosphate | 40 | 15.8 |
| 18 | Ca salt of bis(3-methyl-4-hydroxy-5-t-butylphenyl) sulfide phosphate (×2) | 45 | 15.3 |
| 19 | Mg salt of bis(2,4-di-t-butyl-6-methylphenyl) sulfide phosphate (×2) | 46 | 15.3 |
| 20 | Mg salt of bis(t-C₈H₁₇-phenyl) sulfide phosphate (×2) | 46 | 15.9 |
| 21 | Ba salt of bis(2,4-di-t-butyl-6-methylphenyl)methylene phosphate (×2) | 48 | 14.8 |
| 22 | Na salt of bis(3-methyl-5-t-butyl-phenyl)methylene phosphate | 41 | 16.0 |
| 23 | Ca salt of bis(2,4-di-t-butyl-6-phenyl)biphenyl phosphate (×2) | 44 | 15.7 |
| 24 | Na salt of bis(3,5-dimethylphenyl)methylene phosphate | 43 | 15.2 |

The data show the bis-phenol phosphates of the invention are superior to the Controls.

EXAMPLES 21 TO 25

Low-density polyethylene resin compositions were prepared to the following formulation:

| Ingredient | Parts By Weight |
|---|---|
| Low-density polyethylene resin (Mirason Neo 23H Film grade, Mitsui Polychemical Co., Ltd.) | 100 |
| 4,4-Thiobis(3-methyl-6-t-butyl-phenol) | 0.1 |
| Bis-phenol phosphate shown in Table III | 0.2 |

The ingredients were kneaded at 60° C. for five minutes on a two-roll mill, and then compression-molded for five minutes at 160° C. and 200 kg/cm², and cooled rapidly to 60° C. to obtain specimens 1 mm thick.

The haze value of the specimens was determined according to ASTM D-1003-61, and the results are shown in Table III.

TABLE III

| Example No. | | Haze value (%) |
|---|---|---|
| | Bis-Phenol Phosphate | |
| Control 1 | None | 73 |
| Control 2 | Mg—bis-(2,4-di-t-butylphenyl phosphate) (phenyl phosphate of U.S. Pat. No. | 56 |

TABLE III-continued

| Example No. | | Haze value (%) |
|---|---|---|
| | 4,258,142) | |
| Control 3 | Calcium-p-t-amylphosphate (No. 32 compound of U.S. Pat. No. 4,258,142) | 53 |
| | Phosphates | |
| 28 | 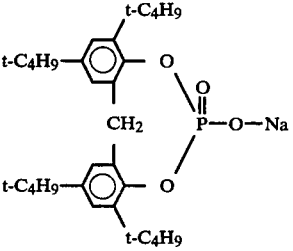 | 41 |
| 29 | 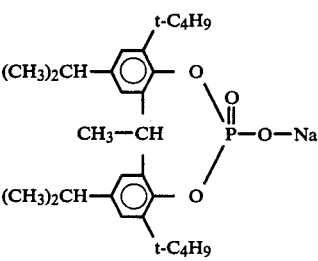 | 43 |
| 30 | 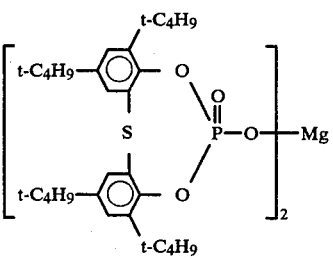 | 45 |
| 31 | 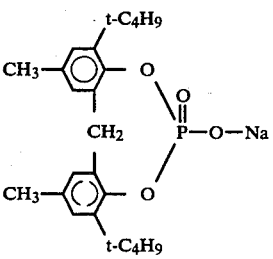 | 42 |
| 32 | 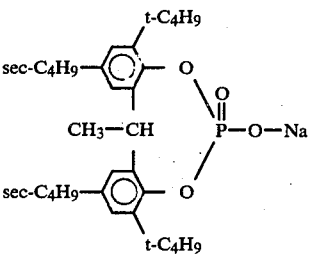 | 43 |

The data show the bis-phenol phosphates of the invention are superior to the Controls.

EXAMPLES 26 TO 29

Polybutene resin compositions were prepared to the following formulation:

| Ingredient | Parts by Weight |
|---|---|
| Polybutene (Film grade M.I. 2.0) | 100 |
| Tetrakis(methylene-3-(3,5-di-t-butyl-4-hydroxyphenyl)propionate)methane | 0.1 |
| Distearyl thiodipropionate | 0.2 |
| Bis-phenol phosphate shown in Table IV | 0.2 |

The ingredients were kneaded on a two-roll mill at 130° C. for five minutes and compression-molded for five minutes at 160° C. and 200 kg/cm², then cooling to 60° C., thus preparing specimens 1.0 mm thick.

The haze value of these specimens was measured according to ASTM D-1003-61, and the results are shown in Table IV.

TABLE IV

| Example No. | Bis-Phenol Phosphate | Haze value (%) |
|---|---|---|
| Control 1 | None | 86 |
| Control 2 | Ca—bis(p-t-butyl phosphate) | 69 |
| | Phosphates | |
| 34 | 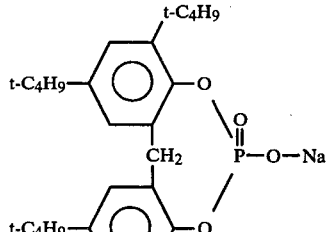 | 57 |
| 35 | 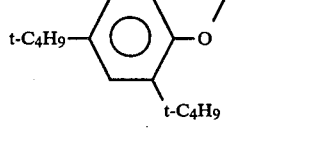 | 60 |
| 36 | 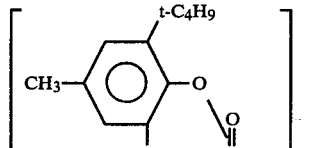 | 56 |

TABLE IV-continued

| Example No. | Bis-Phenol Phosphate | Haze value (%) |
|---|---|---|
| 37 | [structure: bis(2,4-di-t-butylphenyl) phosphate with Ca, ×2] | 60 |

The data show the bis-phenol phosphates of the invention are superior to the Controls.

EXAMPLES 30 TO 34

Compositions were prepared from syndiotactic polybutadiene-1,2, to the following formulation:

| Ingredient | Parts by Weight |
|---|---|
| Syndiotactic-1,2-polybutadiene (JSR RB T814, Japan Synthetic Rubber Co., Ltd.) | 100 |
| Bis-phenol phosphate, shown in Table V | 0.2 |

The ingredients were kneaded at 180° C. for five minutes on a two-roll mill, and then compression-molded for five minutes at 180° C. and 250 kg/cm², then cooled to 60° C. rapidly, to give specimens 1.0 mm thick. The haze value of these specimens was measured according to ASTM D-1003-61, and the results are shown in Table V.

TABLE V

| Example No. | Bis-Phenol Phosphate | Haze value (%) |
|---|---|---|
| Control 1 | None | 54.8 |
| Control 2 | Al tris(-p-t-butylphenyl phosphate) (Phenyl phosphate of Pat. No. 4,258,142) | 44.2 |
| | Phosphates | |
| 39 | 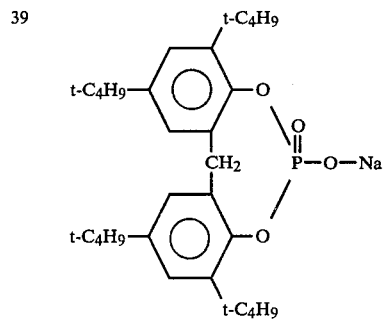 | 14.9 |
| 40 | [structure with C2H5, t-C4H9, CH2 bridge, P-O-Li] | 12.6 |
| 41 | [structure with t-C4H9 groups, S bridge, P-O-Mg, ×2] | 18.6 |
| 42 | [structure with CH3, t-C4H9, P-O-Na] | 14.5 |
| 43 | [structure with t-C4H9 groups, P-O-Ca, ×2] | 17.5 |

The data show the bis-phenol phosphates of the invention are superior to the Controls.

EXAMPLES 35 TO 39

Linear low density polyethylene compositions were prepared to the following formulation:

| Ingredient | Parts by Weight |
|---|---|
| Linear low density polyethylene (ULTZEX 2020L Film grade, Mitsui Petrochemical | 100 |

-continued

| Ingredient | Parts by Weight |
|---|---|
| Industries, Ltd.) | |
| Bis-phenol phosphate shown in Table VI | 0.2 |

The ingredients were kneaded at 140° C. for five minutes on a two-roll mill, then compression-molded for five minutes at 150° C. and 200 kg/cm², and cooled rapidly to 60° C., to obtain specimens 1.0 mm thick.

The haze value of these specimens was measured according to ASTM D-1003-61, and the results are shown in Table VI.

TABLE VI

| Example No. | Bis-Phenol Phosphate | Haze value (%) |
|---|---|---|
| Control 1 | None | 82 |
| Control 2 | Mg—bis-(p-t-butylphenyl phosphate) (Phenyl phosphate of Pat. No. 4,258,141) | 61 |
| 46 | 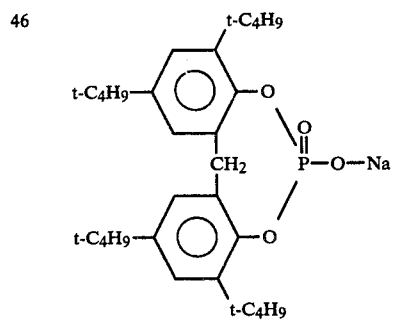 | 50 |
| 47 | 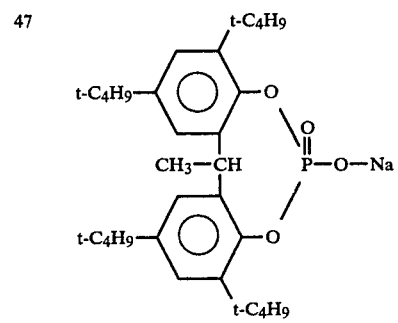 | 51 |
| 48 | 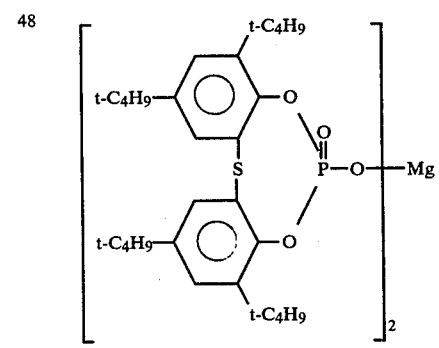 | 53 |

TABLE VI-continued

| Example No. | Bis-Phenol Phosphate | Haze value (%) |
|---|---|---|
| 49 | (structure with CH₃, C₃H₇—CH, P—O—Na) | 55 |
| 50 | (structure with t-C₄H₉ groups, P—O—Ca, bracketed ×2) | 52 |

The data show the bis-phenol phosphates of the invention are superior to the Controls.

EXAMPLES 40 TO 47

Polypropylene compositions were prepared having the following formulation:

| Ingredient | Parts by Weight |
|---|---|
| Unstabilized polypropylene resin (Profax 6501) | 100 |
| Tetrakis (methylene-3-(3,5-di-t-butyl-4-hydroxyphenyl)propionate) methane | 0.1 |
| Dilaurylthiodipropionate | 0.2 |
| Phenol phosphate as shown in Table VII | 0.2 |
| Metal compound as shown in Table VII | 0.3 |

The ingredients were kneaded at 180° C. for five minutes on a two-roll mill, and then compression-molded for five minutes at 180° C. and 250 kg/cm², then cooled to 60° C. rapidly, to give specimens 1.0 mm thick.

The haze value according to ASTMD-1003-61 and Izod impact value at 20° C. were determined for each specimen, and the results are shown in Table VII.

TABLE VII

| Example No. | Phenol Phosphate | Metal compound | Haze value % | Izod impact strength value (Kg/cm/cm) |
|---|---|---|---|---|
| Control 1 | None | None | 83 | 7.5 |
| Control 2 | Di-Na—t-butylphenyl phosphate | None | 58 | 13.2 |

TABLE VII-continued

| Example No. | Phenol Phosphate | Metal compound | Haze value % | Izod impact strength value (Kg/cm/cm) |
|---|---|---|---|---|
| Control 3 | (No. 31 compound of Ohzeki et al U.S. Pat. No. 4,258,142) Di-Na—p-t-butylphenyl phosphate (No. 31 compound of Ohzeki et al U.S. Pat. No. 4,258,142) | Ca stearate | 45 | 15.4 |
| 51 | 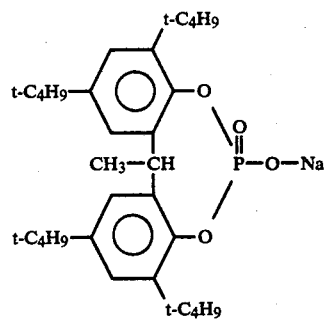 | None | 43 | 16.8 |
| 52 | | Ca stearate | 25 | 17.5 |
| 53 | | Ca laurate | 31 | 17.2 |
| 54 | | Ca octoate | 24 | 17.5 |
| 55 | | Ca benzoate | 29 | 17.3 |
| 56 | | Mg stearate | 34 | 17.1 |
| 57 | | Ba stearate | 40 | 17.0 |
| 58 | | Zn stearate | 41 | 17.0 |

Having regard to the foregoing disclosure, the following is claimed as the inventive and patentable embodiments thereof:

1. Bis-phenol phosphates having the formula:

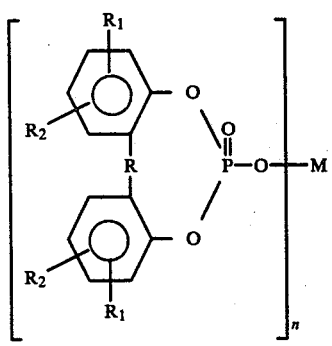

wherein:
R is selected from the group consisting of a carbon-to-carbon bond; thio sulfur —S—; and alkylidene

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to about twelve carbon atoms;
$R_1$ and $R_2$ are each selected from the group consisting of hydrogen, alkyl having from about one to about eighteen carbon atoms; and cycloalkyl having from three to about twelve carbon atoms;
M is a metal atom selected from the group consisting of alkali metal atoms and alkaline earth metal atoms; and
n is the valence of the metal atom M, ranging from one to two.

2. Bis-phenol phosphates according to claim 1 in which R is alkylidene

and $R_1$ and $R_2$ are each alkyl.

3. Bis-phenol phosphates according to claim 1 in which R is thio sulfur —S— and $R_1$ and $R_2$ are each alkyl.

4. Bis-phenol phosphates according to claim 1 in which R is a carbon-to-carbon bond and $R_1$ and $R_2$ are each alkyl.

5. Bis-phenol phosphates according to claim 1 in which R is cycloalkylidene and $R_1$ and $R_2$ are each alkyl.

6. Bis-phenol phosphates according to claim 1 in which $R_1$ and $R_2$ are each t-alkyl and R is alkylidene $$-\overset{R_3}{\underset{R_4}{C}}-.$$

7. Bis-phenol phosphates according to claim 1 in which R is a carbon-to-carbon bond.

8. Bis-phenol phosphates according to claim 1 in which R is thio sulfur —S—.

9. Bis-phenol phosphates according to claim 1 in which R is alkylidene

10. Bis-phenol phosphates according to claim 9 in which $R_3$ and $R_4$ are each hydrogen.

11. Bis-phenol phosphates according to claim 9 in which $R_3$ is hydrogen and $R_4$ is alkyl.

12. Bis-phenol phosphates according to claim 9 in which $R_3$ is hydrogen and $R_4$ is cycloalkyl.

13. Bis-phenol phosphates according to claim 9 in which $R_3$ and $R_4$ are taken together as cycloalkylidene.

14. Bis-phenol phosphates according to claim 1 in which M is an alkali metal.

15. Bis-phenol phosphates according to claim 1 in which M is an alkaline earth metal.

16. Bis-phenol phosphates according to claim 1 in which M is a polyvalent metal.

17. Bis-phenol phosphates according to claim 1 in which $R_1$ and $R_2$ are each tertiary alkyl.

18. Bis-phenol phosphates according to claim 1 in which $R_1$ is hydrogen and $R_2$ is tertiary alkyl.

19. Bis-phenol phosphates according to claim 1 in which $R_1$ is hydrogen and $R_2$ is cycloalkyl.

20. An α-olefin polymer composition having improved clarity comprising a polymer of an α-olefin having two to six carbon atoms and an amount to improve clarity of at least one bis-phenol phosphate having the formula:

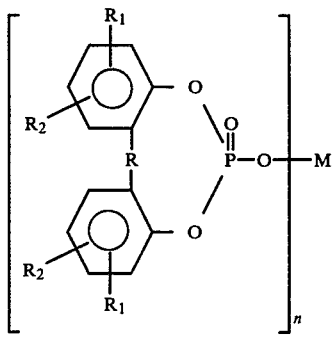

wherein:

R is selected from the group consisting of a carbon-to-carbon bond; thio sulfur —S—; and alkylidene

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to about twelve carbon atoms;

$R_1$ and $R_2$ are each selected from the group consisting of hydrogen, alkyl having from one to about eighteen carbon atoms; and cycloalkyl having from three to about twelve carbon atoms;

M is a metal atom selected from the group consisting of alkali metal atoms and alkaline earth metal atoms; and n is the valence of the metal atom M, ranging from one to two.

21. An α-olefin polymer composition according to claim 20 in which the olefin polymer is polypropylene.

22. An α-olefin polymer composition according to claim 20 in which the olefin polymer is polyethylene.

23. An α-olefin polymer composition according to claim 20 in which the olefin polymer is poly-1-butene.

24. An α-olefin polymer composition according to claim 20 in which the quantity of bis-phenol phosphate is within the range from 0.005 to 5 parts by weight per 100 parts by weight of α-olefin polymer.

25. An α-olefin polymer composition having improved clarity comprising a polymer of an α-olefin having two to six carbon atoms and an amount to improve clarity of at least one bis-phenol phosphate according to claim 2.

26. An α-olefin polymer composition having improved clarity comprising a polymer of an α-olefin having two to six carbon atoms and an amount to improve clarity of at least one bis-phenol phosphate according to claim 3.

27. An α-olefin polymer composition having improved clarity comprising a polymer of an α-olefin having two to six carbon atoms and an amount to improve clarity of at least one bis-phenol phosphate according to claim 4.

28. An α-olefin polymer composition having improved clarity comprising a polymer of an α-olefin having two to six carbon atoms and an amount to improve a clarity of at least one bis-phenol phosphate according to claim 5.

29. An α-olefin polymer composition having improved clarity comprising a polymer of an α-olefin having two to six carbon atoms and an amount to improve clarity at at least one bis-phenol phosphate according to claim 8.

30. A stabilizer composition for improving the clarity of polymers of α-olefins having two to six carbon atoms, comprising a heat or light stabilizer for α-olefin polymers and a bis-phenol phosphate having the formula:

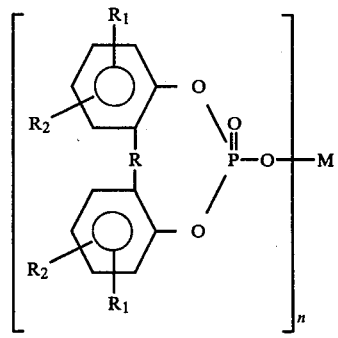

wherein:

R is selected from the group consisting of a carbon-to-carbon bond; thio sulfur —S—; and alkylidene

in which $R_3$ and $R_4$ are selected from the group consisting of hydrogen, alkyl having from one to about eighteen carbon atoms, and cycloalkyl, including cycloalkylidene in which $R_3$ and $R_4$ are taken together as part of a cycloalkylene ring, having from three to about twelve carbon atoms;

$R_1$ and $R_2$ are each selected from the group consisting of hydrogen, alkyl having from one to about eighteen carbon atoms; and cycloalkyl having from three to about twelve carbon atoms;

M is a metal atom selected from the group consisting of alkali metal atoms and alkaline earth metal atoms; and n is the valence of the metal atom M, ranging from one to two.

31. A stabilizer composition according to claim 30 in which the heat stabilizer is selected from the group consisting of phenolic antioxidants, organic phosphites and thio ethers.

32. A stabilizer composition according to claim 30 in which the light stabilizer is selected from the group consisting of 2,2,6,6-tetraalkyl piperidinyl compounds, benzophenones and bis-(2,2,6,6-tetramethyl-4-piperidyl) sebacate.

* * * * *